United States Patent [19]
Herbert et al.

[11] Patent Number: 5,806,335
[45] Date of Patent: Sep. 15, 1998

[54] COLD THERAPY DEVICE

[75] Inventors: H. Nicholas Herbert, San Juan Capistrano; Elias Montenegro, South Gate, both of Calif.

[73] Assignee: Pabban Development Inc, Irvine, Calif.

[21] Appl. No.: 800,167

[22] Filed: Feb. 13, 1997

[51] Int. Cl.$^6$ .................................................. F25D 17/02
[52] U.S. Cl. ............................ 62/434; 62/259.3; 607/114
[58] Field of Search .................................. 62/259.5, 430, 62/439, 99, 59, 185; 607/96, 104, 108, 114; 604/291

[56] References Cited

U.S. PATENT DOCUMENTS

| | | | |
|---|---|---|---|
| 2,726,658 | 12/1955 | Chessey | 62/259.3 |
| 3,248,897 | 5/1966 | Stark | 62/259.3 |
| 4,596,120 | 6/1986 | Knodel et al. | 62/434 |

Primary Examiner—John M. Sollecito
Attorney, Agent, or Firm—G. Donald Weber, Jr.

[57] ABSTRACT

A cold temperature therapy device for use on localized areas of the human body. The device includes a flexible, pliable liquid circulating pad which may be readily conformed to a portion of the human body. The pad is connected to a liquid source via a suitable pumping or liquid moving device which supplies liquid to the pad. The liquid moving device may be manual or powered. The liquid is, effectively, stored in a measurement tray which is disposed adjacent to a cooling unit. The apparatus (with the exception of the pad, the manual pump and the connecting conduits) is maintained in a carrying case which can be insulated to enhance the operation of the cooling device.

20 Claims, 2 Drawing Sheets

COLD THERAPY DEVICE

BACKGROUND

1. Field of the Invention

This device is directed to cooling devices, in general, and to cooling devices which are used to provide cold temperature therapy to localized areas of the body, in particular.

2. Prior Art

There are many types of cooling devices known in the art. In particular, there are many devices which are used to cool parts of the human body as a type of therapy.

In the particular field of the instant invention, these devices include spray devices which spray material such as ethylchloride onto areas of the body to provide instanteous, localized numbing of an injured body portion. These devices normally provide a very short term relief.

Alternatively, there are also known in the art packages which contain a liquid or semi-liquid material such as a gel, foam or refrigerant which packages are, typically, stored in a freezer in order to freeze the material. The package is removed from the freezer and applied to the portion of the body which has been traumatized and requires therapy. These packages usually provide relief for a limited time. Moreover, they tend to be awkward and messy to use.

In addition, there are other devices known in the art which use pads which are placed against the traumatized body portion and which utilize fluid circulation therethrough. Such devices are described in U.S. Pat. Nos. 4,149,541; 5,086,771; and/or 5,417,720. However, these patents are all directed to devices which have specified and specific designs of the pad while requiring cumbersome, expensive and inefficient means for cooling the fluid which circulates through the pad.

SUMMARY OF THE INSTANT INVENTION

The invention is directed to a quick starting, portable cold temperature therapy device for use on localized areas of the human body. The device is a continuously regulated unit which provides consistent coldness. The device includes a flexible, pliable pad which may be readily conformed to a portion of the human body. The pad is hollow and is connected to a liquid source via a suitable, typically insulated, conduit. A manual or powered pumping device circulates the liquid which is, thus, supplied to the pad. The liquid is, effectively, stored in a tray which is disposed adjacent to a cooling unit. A carrying case formed of an insulating material can be provided to enhance the operation of the cooling device.

DESCRIPTION OF A PREFERRED EMBODIMENT

Figure 1:
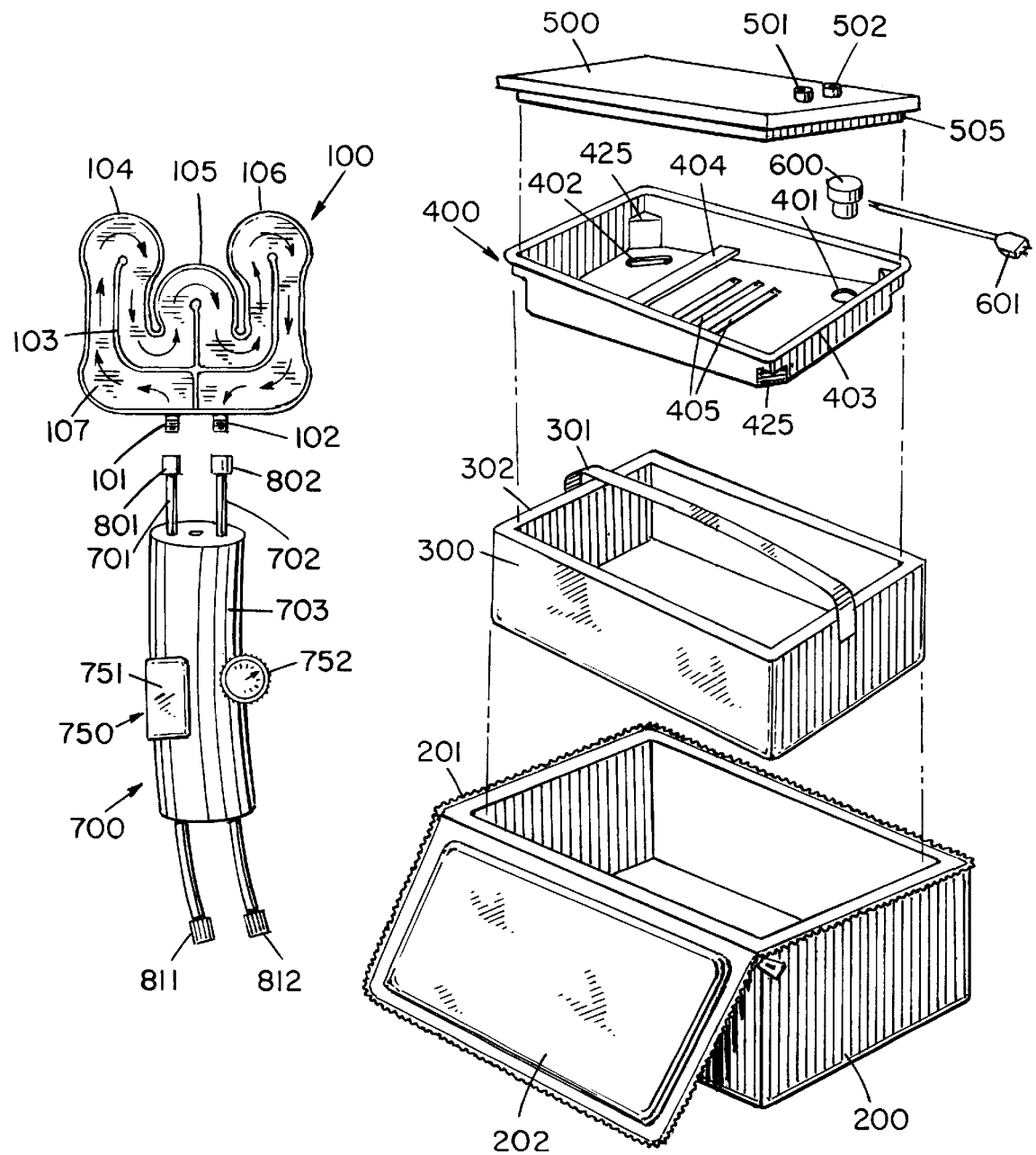
FIG. 1 is an exploded view of a powered pump embodiment of the instant invention

Referring now to FIG. 1, there is shown an exploded view of one embodiment of the cold therapy device 10 of the instant invention.

The device (or system) includes a plastic bag or pad 100. In this instance, the pad is formed of a water impervious outer skin or layer of a flexible plastic or synthetic polymeric film material such as poly vinyl chloride which is sealed at the edges thereof. The pad 100 includes an internal partition 103 at portions thereof. The partition 103 is joined to inner surfaces of the upper and lower faces of pad 100 in order to establish a flow path for the fluid as described hereinafter. The pad 100 includes three substantially parallel fingers 104, 105 and 106 connected together in a common base 107 at one end thereof. The internal partition 103 is disposed at approximately the middle of each of the fingers as well as the common base.

Connectors 101 and 102 are provided at the edge of the pad 100 on opposite sides of the internal partition 103 in the common base 107. Thus, fluid which is supplied to the pad 100 passes through the inlet connector 101, through fingers 104, 105 and 106, respectively, as controlled by the internal partition 103 and out the outlet connector 102. In a preferred embodiment, the connectors 101 and 102 are both conventional male plug connectors which include unidirectional shut-off valves therein. That is, when the connectors are not connected to a source, the shut-off valves prevent flow through the connectors. Of course, the connectors 101 and 102 can both be female receptacle connectors or one male and one female, if so desired.

A pair of tubular conductors 701 and 702 are provided. These conductors are arranged to interact with and connect to the connectors 101 and 102, respectively. More particularly, connectors 801 and 802 are disposed on the ends of conduits 701 and 702. Connectors 801 and 802 are complementary to connectors 101 and 102, respectively. Thus, if connector 101 is a male connector, connector 801 is a female connector and so forth. Connectors 801 and 802 also include shut-off valves to prevent fluid flow when the connectors are not joined together.

Typically, the conductors 701 and 702 are fabricated of a flexible plastic material such as polyvinyl chloride (PVC). A sheath 703 of insulating material is disposed around the pair of conductors 701 and 702 in order to maintain the conductors in a compact conduit arrangement 700. In addition, the sheath 703 (which can incorporate an individual sheath for each conductor), when fabricated of an insulating foam material, inhibits the heating or cooling (by ambient conditions) of the contents or fluid which is flowing through conductors 701 and 702. Appropriate connectors 811 and 812 are provided at the other ends of conductors 701 and 701, as well.

An insulating carrying case 200 is provided. The carrying case is fabricated of a suitable insulating material such as foam or the like as is known in the art and is used to insulate other containers such as picnic baskets or the like. In a preferred embodiment, the outer material for the insulating case can be nylon or other suitable material. This material is formed as a carrying case which may be collapsible, if so desired.

The case includes a top 202 which is, typically, hingedly attached to the case 200. In a preferred embodiment, a zipper 201 is provided at the edges of the case 200 and the lid 202 in order that the lid and case can be selectively joined together (or opened) as a result of the operation of the zipper 201.

A chest 300 is formed of a sturdy, lightweight, leak-proof material such as polypropylene. The chest 300 is intended to be inserted into the insulating carrying case 200. Typically, the chest 300 is open at the top and includes a lip or upper edge 302 which will receive a tray described hereinafter and provide a fluid seal therewith.

In one embodiment, a strap 301 is affixed to opposing sides of the chest 300 (in any suitable manner) adjacent the upper edge 302 thereof. The strap 301 is used for carrying the chest or lifting the chest into and out of the carrying case 200. The strap 301 can be made of any suitable material such as plastic or the like, and can be affixed to the chest in any suitable fashion such as a rivet or the like.

A tapered tray 400 is formed of a strong, lightweight, water plastic material such as ABS plastic. The tray 400, which can be vacuum formed or the like, is dimensioned to fit fairly snugly within the chest 300. Typically, a lip 403 is formed around the upper edge of the tray 400 to rest upon the upper edge 302 (or lip) of chest 300 so that the tray extends about ⅓ of the depth into the chest. In a preferred embodiment, the tray 400 includes a stepped inserts 425 in each corner. The steps permit the chests (and trays) to be stacked together, if desired. In addition, the steps 425 can be included to add strength to tray 400.

The tray 400 has a tapered or sloping configuration wherein one end is deeper than the other to induce fluid or liquid flow from the shallow end towards the deep end. In a preferred embodiment, one or more ribs 405 can be included in the surface of the tray.

Holes 401 and 402 are placed in the shallow end and deep end of the tray 400, respectively. In addition, a slot 404 is formed or cut into tray 400 from side-to-side about ⅓ of the distance from the deep end of the tray.

A lid 500 is fabricated of a suitable lightweight, strong, water impervious and flame retardant plastic material such as ABS plastic. The lid 500 is adapted to overlie the tray 400 and to form a seal with the edges thereof which prevents (or at least inhibits) fluid or liquid flow over the sides of the tray. The lid includes a central portion 505 which is thicker than the lid 500, per se, and is adapted to provide a housing and/or support for a powered pump, as described hereafter. In addition, connectors 501 and 502 extend through the lid 500 in order to interconnect with the pump and liquid therein. In addition, the connectors 501 and 502 are adapted to connect with the connectors 811 and 812 of conductors 701 and 702 as described supra in order to supply the liquid to the pad 100.

Of course, it is contemplated that the chest 300 and/or lid 500 can be made of a suitable insulating material. In this arrangement, the case 200, the chest 300 and the lid 500 can be integrally formed as a single unit.

The pump 600 is any conventional pumping mechanism (i.e. centrifugal, peristaltic or the like) which is properly sized and dimensioned so that it will fit within the enlarged central portion 505 of lid 500. The pump is adapted to connect to at least one of the connectors 501 and 502 to pump the fluid or liquid therethrough to conductors 701 and 702 as suggested supra. The other one of connectors 501 and 502 can merely permit the fluid or liquid to drain into tray 400.

The pump 600 is adapted to be connected to a suitable power source, such as a conventional AC or DC source, a battery, or, as shown, a low voltage adapter 601. In the case of such an arrangement, a circuit breaker or fused line can be provided. This feature will prevent the unit from starting a fire in the unlikely event that a short circuit occurs. The circuit breaker will interrupt the current in the electric circuit when the current becomes too high. Of course, fuses must be replaced after use. However, a circuit breaker can be reset after it has been tripped.

In operation, the lip 403 of tray 400 is placed on the upper edge 302 of the chest 300. Water or other suitable liquid is put into chest 300 by pouring the liquid into tray 400 so that the liquid drains through opening 402 and/or slot 404. The chest 300 is considered to be filled until the liquid reaches the level equivalent to opening 402. The chest 300 is then placed in a freezer until the water in the chest freezes. The chest and the frozen contents are stored in a freezer until needed.

In application of the system, the tray 400 (and part of chest 300) are then filled with water, again, up to opening 401 in tray 400. Thus, there is a quantity of water in the tray. Thus, water is, to some extent, in contact with the frozen contents of chest 300. The tray 400 and chest 300 are then placed in carrying case 200 (if not previously so placed). The lid 500 and top 202 are then placed onto the tray and forms a watertight seal therewith. The connectors 801 and 802 of conductors 701 and 702 are coupled to the connectors 101 and 102, respectively, of pad 100. The conductors 701 and 702 are connected to connectors 501 and 502 via connectors 811 and 812, respectively. The pump 600 is then activated to cause the liquid in tray 400 to be pumped through the conduit 700. Of course, any set of connectors may be preconnected during assembly of the apparatus.

In a preferred embodiment, a thermostatic control 750 can be mounted on the conductors 701 or 702 which can control the water flow of pump 600 as a function of the temperature of the fluid or liquid which passes therethrough. For example, a thermostat 751 can be placed adjacent to conductor 701 to detect the temperature of the liquid flowing in the conductor. A flow valve 752 can be installed in conductor 752 to be manually or automatically adjusted as a function of the reading detected in the thermostat 751. Thus, the termperature of the liquid in pad 100 can be controlled.

Thus, the circulating water stored in the tray 400 is moved through the unit by the pump and comes in direct contact with the solid block of ice in chest 300. The heat exchange rate is such that the circulating water can be cooled to slightly above freezing temperature in a very short span of time. When the container is proportioned to be approximately 183 cubic inches (i.e. about three liters of water), the system will provide approximately 8 hours of continuous cold therapy.

Figure 2:
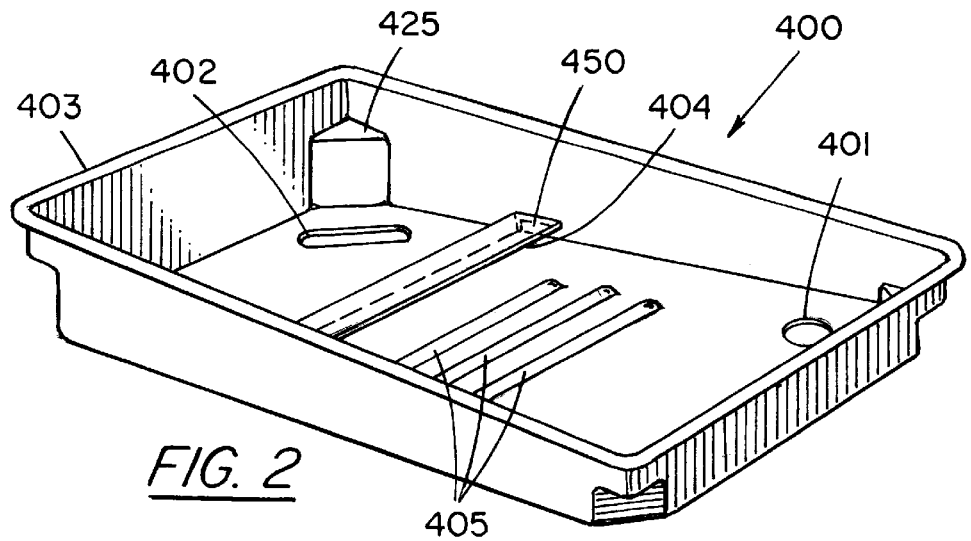
FIG. 2 is a detailed view of the storage tray of the instant invention.

Referring now to FIG. 2, there is shown a detailed representation of a portion of tray 400 shown in FIG. 1. FIG. 2 also shows specific implementations which may be incorporated into the system. For example, holes 401 and 402 may be included in the tray 400 to indicate to the user how much water is to be placed in the tray. The amount of water in the tray can influence the rapidity at which the circulating water reaches the desired temperature and the reverse heat exchange principle with regard to the melting of the ice in chest 300. Of course, the holes 401 and 402 permit the water to be pumped through the system as described.

In addition, the ribs 405 (which can take any suitable configuration) create turbulence in water flowing through tray 400 during operation of the system. This turbulence tends to expedite the cooling of the water in tray 400 by the ice in chest 300.

Likewise, the slot 404 can be incorporated in the bottom of tray 400. The slot 404 permits liquid to flow into chest 300 into contact with the ice block therein. This operation facilitates and expedites the cooling (chilling) of the water being pumped through the system and into pad 100.

As shown in FIG. 2, a grip 450 can be formed as a part of tray 400. That is, tray 400 (which can be a vacuum formed plastic unit) can include the grip 450 which is used as a handle to remove tray 400 from the chest 300 or case 200.

In this arrangement, the grip 450 can be formed downstream from slot 404 and act as a guide to insure that the water flows through slot 404. The grip can be dimensioned so as to not interfere entirely with water flow in tray 400. Likewise, the grip 450 can include one or more apertures therein so as to be permeable to the flow of water from the shallow end to the deep end of tray 400.

In an alternative embodiment, tray 400 may be selectively fastened (or fastenable) to chest 300 by screws or the like. In this embodiment, the grip 450 can be used in lieu of strap 301 in order to conveniently manipulate the tray and the chest.

While a tapered or sloping tray 400 is a preferred embodiment in order to insure water flow, it is contemplated that tray 400 can have a relatively flat bottom. In this arrangement, the water flow in the tray 400 is produced as a result of the pressure applied to the water by the pump mechanism.

Figure 3:
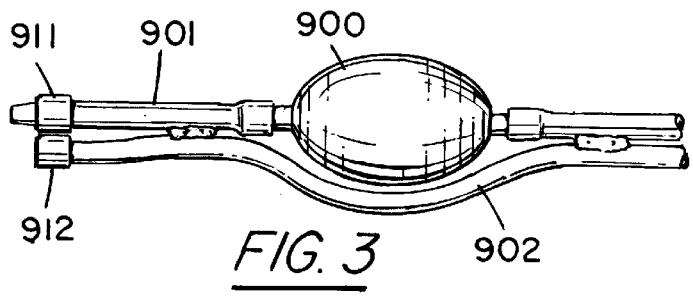
FIG. 3 is a schematic representation of a manual pump embodiment of the instant invention.

Referring now to FIG. 3, there is shown an alternative embodiment of the instant invention. This embodiment is substantially similar to the system shown in FIG. 1 except as regards the pump mechanism. The embodiment shown in FIG. 3 shows a manual pump 900 which can be used in conjunction with, or in lieu of, the powered pump 600.

In particular, a conventional hollow squeeze bulb 900 is inserted in-line in conductor 901 which is similar to conductor 701 shown in FIG. 1. Conductor 902 (similar to conductor 702) remains a unitary conductor.

In this embodiment, the user of the system manually operates (squeezes) bulb 900 to effect the pumping action in the system. Thus, specific control of the system can be achieved. Likewise, the system can be operated in the absence of a suitable power source.

In this embodiment, the bulb 900 may be connected to conductor 901 by connectors of the type described supra whereby the bulb 900 (like pad 100) can be removed from the system, if so desired, without leakage of liquid.

Also, as shown in FIG. 3, the conductor 901 has a male connector 911 on an end thereof. The associated end of conductor 902 has a female connector 912 thereof. While not required, this "polarized" or specific designation of the method of connection to complementary connections 101 and 102 in pad 100 assures proper flow direction of the therapy fluid in the system.

Figure 4:
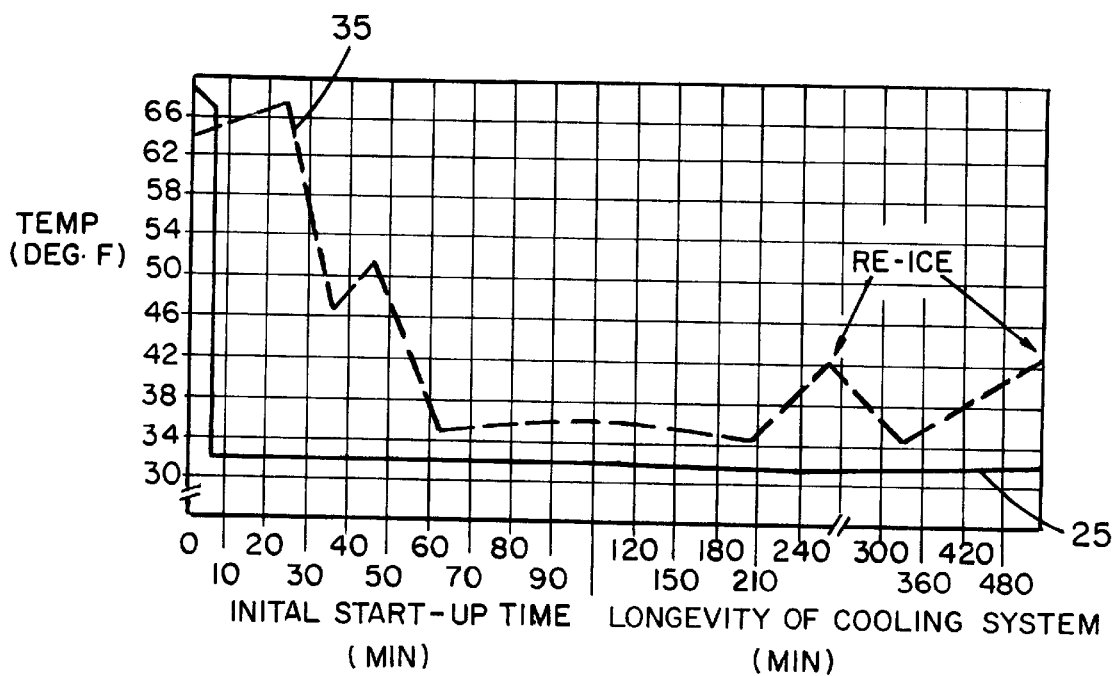
FIG. 4 is a time/temperature chart of the operation of the instant invention.

Referring now to FIG. 4, there is shown a time vs temperature chart of the operation of the preferred embodiment of the instant invention. To illustrate the advantageous operation of the invention, the operation of competitive ice cube cold therapy systems is plotted on the same chart.

The operation of the instant invention is depicted by solid line 25. In this case, typical tap water at approximately 60° F. is placed in tray 300 (after the system has been properly prepared as described above). Within 10 minutes (typically 5–8 minutes), the water in the system and, thus, in the pad 100 is at about 33° F. This cold water is circulated through the system as described supra. The circulating water remains substantially constant at about 33° F. for approximately 8 hours.

Conversely, the existing prior art system is depicted by dashed line 35. This water is assumed to be at or about 64° F. at the start. The temperature of the water does not begin to cool for nearly 25 minutes. The cooling continues slowly until the cool water reaches about 36° F. after approximately an hour. This cooled water remains fairly constant for about 3.5 to 4 hours. At that time, the prior art devices require the cooling system to be re-iced. Even still, the water temperature tends to rise dramatically. Thus, the embodiment of the invention provides a significant improvement over the prior art.

It should be understood that the connectors described above can take many forms. Also, various combinations of connectors can be utilized. In some cases, the connections of components can be integral portions of the components wherein detachable connectors are not required. Thus, the specific types of connectors and the arrangements thereof are, to some extent, design considerations.

Thus, there is shown and described a unique design and concept of cold therapy device. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

We claim:

1. A therapy system comprising
   a first storage container for storing a temperature controller material therein,
   said first storage container comprises a generally rectilinear receptacle with an interior space,
   a second storage container which is adapted to be placed within said first storage container and to communicate with the interior space thereof such that fluid material can flow from said second storage container into said first storage container to contact said temperature controller material,
   pump means which communicates with said second storage container to pump fluid material therefrom, and
   a third storage container connected to said pump means to receive said fluid material from said second storage container wherein said third storage container comprises a pad which is adapted to conform to the human body for therapeutic treatment thereof.

2. The system recited in claim 1 wherein,
   said pump means is manually operated.

3. The system recited in claim 1 wherein,
   said second storage container comprises a tray with a variable depth to enhance the flow of fluid material therein into the interior space of said first storage container.

4. The system recited in claim 1 wherein,
   said pad comprises a deformable pouch.

5. The system recited in claim 1 wherein,
   said fluid material is water.

6. The system recited in claim 1 including,
   conduit means connected between said second and third storage containers to conduct fluid therebetween.

7. The system recited in claim 1 wherein,
   said material is ice.

8. The system recited in claim 1 including,
   a carrying case for receiving said first and second storage containers.

9. The system recited in claim 8 wherein,
   said carrying case is formed of a thermally insulating material.

10. The system recited in claim 8 wherein, said carrying case includes a cover which is selectively joined thereto.

11. The system recited in claim 1 wherein, said first storage container is open at the top to receive said second storage container in a nesting arrangement.

12. The system recited in claim 1 including, lid means which overlies and seals said second storage container.

13. The system recited in claim 12 wherein, said pump means is mounted in said lid means.

14. The system recited in claim 1 wherein, said first storage container is fabricated of thermally insulating material.

15. The system recited in claim 1 including, a power source selectively connected to said pump means to cause said pump means to be operative.

16. The system recited in claim 4 wherein, said pouch includes upper and lower faces joined together to form a liquid tight container, said upper and lower faces are formed with three adjacent compartments.

17. The system recited in claim 16 wherein, said pouch includes internal partitions which form a continuous flow pattern through all of said compartments.

18. The system recited in claim 3 wherein, said second storage container includes at least one uneven surface to inhibit freezing of fluid on said uneven surface.

19. The system recited in claim 1 including, temperature detection means for detecting the temperature of said fluid material in said system.

20. The system recited in claim 1 including, flow control means to control the flow of said fluid material from said second storage container via said pump means.

* * * * *